United States Patent [19]

Hewson

[11] Patent Number: 5,036,848
[45] Date of Patent: Aug. 6, 1991

[54] METHOD AND APPARATUS FOR CONTROLLING BREATHING EMPLOYING INTERNAL AND EXTERNAL ELECTRODES

[75] Inventor: Carl E. Hewson, Marshfield, Mass.

[73] Assignee: Brunswick Biomedical Technologies, Inc., Wareham, Mass.

[21] Appl. No.: 421,807

[22] Filed: Oct. 16, 1989

[51] Int. Cl.⁵ ............................................. A61N 31/00
[52] U.S. Cl. ................................ 128/419 G; 128/421; 128/642
[58] Field of Search .................... 128/419 G, 784, 421, 128/642

[56] References Cited

U.S. PATENT DOCUMENTS

| | | | | |
|---|---|---|---|---|
| 2,532,788 | 12/1950 | Sarnoff | ............................ | 128/419 G |
| 3,955,583 | 5/1976 | Hörauf | ............................. | 128/420 R |
| 4,301,794 | 11/1981 | Tapper | .................................. | 604/20 |
| 4,683,890 | 8/1987 | Hewson | ........................... | 128/419 G |

FOREIGN PATENT DOCUMENTS 1410761 10/1975 United Kingdom ............ 128/419 G

Primary Examiner—William E. Kamm
Assistant Examiner—Scott M. Getzow
Attorney, Agent, or Firm—Wolf, Greenfield & Sacks

[57] ABSTRACT

A method of stimulating breathing which comprises the steps of positioning a non-invasive internal electrode in the esophagus and two external electrodes on the chest. A pulsed stimulation of approximately two seconds duration is interposed across the electrodes with a magnitude of the successive pulses in each stimulation increasing linearly. An interval of approximately three seconds is interposed between successive stimulations. In a preferred embodiment of the invention, the polarity of successive electrical stimulations is reversed.

13 Claims, 3 Drawing Sheets

5,036,848

METHOD AND APPARATUS FOR CONTROLLING BREATHING EMPLOYING INTERNAL AND EXTERNAL ELECTRODES

RELATED APPLICATION

This application is directed to an improvement over the invention forming the subject of my U.S. Pat. No. 4,683,890 dated Aug. 4, 1987 entitled Method and Apparatus for Controlled Breathing Employing Internal and External Electrodes.

INTRODUCTION

This invention relates to a method and apparatus for ventilating patients. When a person's breathing stops due to cardiac arrest or fibrillation, or he suffers respiratory depression from such causes as drug overdose, smoke inhalation, drowning etc., or breathing stops for any other reason, it is imperative to reinstate breathing as a life saving measure as well a to avoid brain damage due to oxygen deficiency.

The normal method of artificially ventilating a patient is to blow air into the lungs in a rhythmic fashion either by mouth to mouth or using an oxygen powered demand valve and mask. Both of these well-known techniques have been used successfully countless times, but they have certain disadvantages. These techniques create positive pressure in the lungs of the patient being ventilated, and the positive pressure can impair blood flow to the lungs and the return of the blood supply to the heart.

One important object of the invention of my earlier U.S. Pat. No. 4,683,890 as well of the present invention is to provide a method and apparatus for ventilating patients which mirrors the normal breathing cycle so as not to inhibit blood flow in the lungs and to the heart.

Another important object of this as well as my earlier invention is to provide a non-invasive technique for electrically stimulating natural ventilation.

My earlier paten teaches that by the proper placement of electrodes on the chest and in the esophagus and by supplying a controlled electrical impulse, the diaphragm muscles may be stimulated to expand the lungs creating negative pressure causing air to fill the lungs. This is the normal breathing process, and it does not inhibit blood flow in the lungs and to the heart. In accordance with the earlier invention an internal electrode is passed down the esophagus. The electrode is a tube or rod having a flexibility similar to a normal commercial gastric tube and has series of circumferential electrical contact rings spaced few centimeters apart but all electrically connected. Two external electrodes electrically connected together, and each a commercially available ECG electrode, are placed one left and one right on the body of the patient in the region of the nipples above the rib cage. Between the internal and two external electrodes is passed a selectable pulsed current up to 100 milliamperes selectively delivered at from 10 to 18 cycles per minute. A typical pulse for a rate of 12 pulses per minute would be a linear rise from zero output to maximum output in 2 seconds followed by a zero output for the next three seconds. The cycle is repeated so long as the stimulation is needed. The electrical circuit is battery operated and the device may be handheld.

The present invention is a further development to more effectively induce normal breathing in a patient whose breathing has stopped. In accordance with this invention, the linearly increasing two second stimulations are replaced with spiked pulses having an on-off duration in the order of 0.1 millisecond "on" and 1.0 milliseconds off and constantly increasing linearly in magnitude over the two second period. As in the earlier invention, the two second "stimulation" period is followed by an "off" period of three seconds. Tests have revealed that the constant application of an increasing voltage can tire the chest muscles and cause muscle degeneration due to absorption, and the present invention avoids or markedly lessens those problems. Also in accordance with the present invention, the polarity of the pulses in each successive two second stimulation may advantageously be reversed When this is not done, continued stimulation causes the accumulation of a charge in the muscles so that the muscle responses are of decreasing magnitude. This can be counteracted by reversing the polarity of pulse stimulations, either successively with each cycle, or at some lesser frequency.

I have also discovered that most effective ventilation may be achieved by placing the external electrodes at the region of the fourth ribs.

These and other object and features of this invention will be better understood and appreciated from the following detailed description of different embodiments thereof, selected for purposes of illustration and shown in the accompanying drawings.

BRIEF FIGURE DESCRIPTION

DETAILED DESCRIPTION

The action of breathing, which consists of two functions, namely inspiration and exhalation, may be described as follows:

The diaphragm is the principal muscle of inspiration. When in a condition of rest the muscle presents a domed surface, concave toward the abdomen and consists of circumferential muscle and a central tendinous part. When the muscle fibers contract, they become less arched, or nearly straight, and thus cause the central tendon to descend and become a fixed point which enables the circumferential muscles to act from it and so elevate the lower ribs and expand the thoracic cavity. The ordinary action of expiration or exhalation is hardly effected by muscular forces but results from a return of the walls of the thorax to a condition of rest owing to their own elasticity and to that of the lungs.

(See Anatomy by Henry S Gray, Bounty Books, published in 1977, page 555.)

The present invention artificially stimulates the diaphragm muscle to duplicate the action which occurs naturally in a healthy person.

Figure 1:
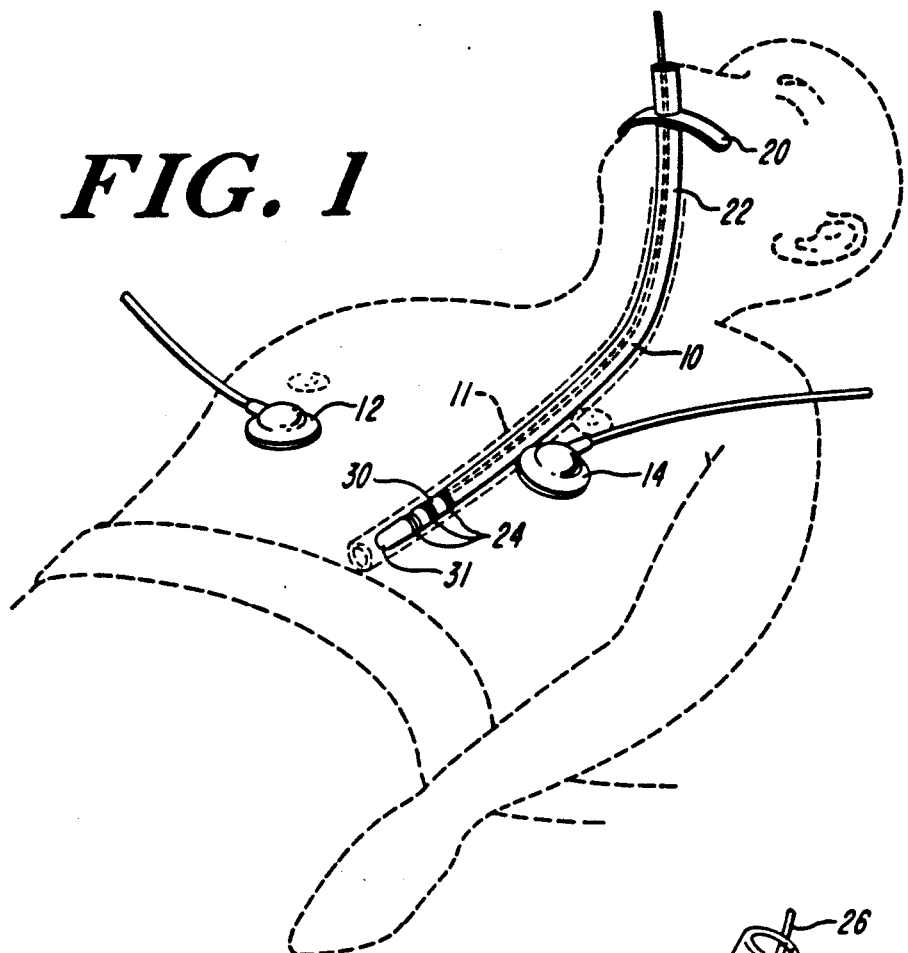
FIG. 1 is a cross sectional view, somewhat diagrammatic, of the head and chest of a patient and showing the use of the present invention.

FIG. 1 depicts a patient being assisted by the ventilating system of the present invention. A first electrode 10 is shown disposed in the patient's esophagus 11 and a pair of external electrodes 12 and 14 are shown placed on the patient's chest on the left and right sides in the region of the base of the rib cage, and more specifically above the fourth ribs. The electrodes are all connected to an electrical circuit 16 which impresses a pulsed stimulation between the internal electrode 10 and the external electrodes 12 and 14 through the chest muscle of the patient. When the muscle is stimulated, it contracts so as to elevate the lower ribs and expand the thoracic cavity, which effects a reduction in pressure, in turn causing inspiration. When the stimulation is removed, the walls of the thorax return to the rest condition causing exhalation.

Figure 2:
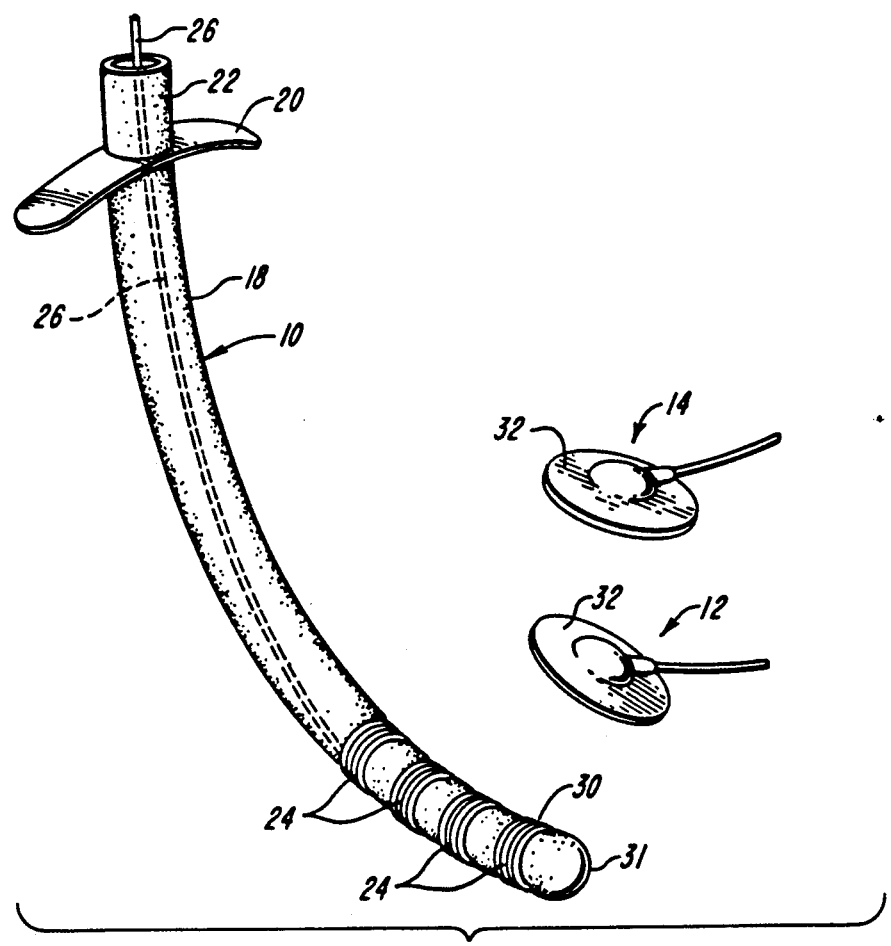
FIG. 2 is a perspective view of the invention shown in FIG. 1.

In FIGS. 1 and 2 the electrode 10 is shown to include a curved tubular body 18 which is shaped to be inserted directly into the patient s esophagus without the aid of a larger tubular member serving as a guide for that purpose. It is to be understood, however, that the system of the present invention may be used in combination with other apparatus and it is contemplated that the electrode 10 in certain situations may be guided into the esophagus through a previously inserted tube such as a gastric tube. The electrode 10 carries a stop 20 adjacent to its proximal end 22 which may be used to limit the depth of penetration of the electrode 10 into the esophagus. The stop 20 should not cover the mouth or otherwise interfere with the passage of air to and from the lungs. The body 18 of the electrode preferably is somewhat flexible in the nature of a commercially available gastric tube so that it may be inserted in the esophagus and will not injure the esophagus lining. It may or may not call for the use of lubricant. Moreover the electrode may be inserted through the mouth or nose. The electrode may be identical to that shown in U.S. Pat. No. 4,574,807 issued Mar. 11, 1986 entitled Heart Pacer, which patent has a common assignee with this application.

Figure 3:
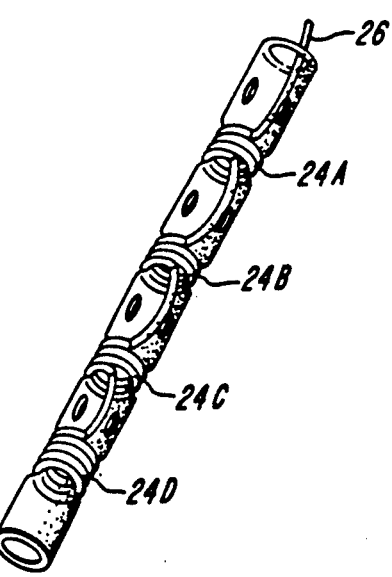
FIG. 3 is an enlarged perspective view of the distal end of the internal electrode forming part of this invention.

In FIG. 3 the distal end of the electrode 10 is shown in detail. It includes four contact rings 24 embedded in its surface. While four rings are shown, a lesser or greater number may be used. The contact rings in the embodiment shown are formed from a continuous length of tinned copper wire 26 which is connected to a post contact 28 shown on the proximal end 22 of the body 18 and which in turn is connected during use to the electrical control system 16. The wire 26 extends inside the body 18 to first ring contact 24A in turn formed by several turns of wire on the surface of the body 18. The wire again enters the body 18 beyond the contact 24A and reemerges at the next ring contact 24B also formed by several additional turns of the wire. The third and fourth ring contacts 24C and 24D are similarly formed and connected to one another by the wire inside the body. Thus, the four electrode contacts are connected in series and formed from a single length of wire. Typically, each of the ring contacts may be 0.2 inch in length and they may be spaced one inch apart. The wire may typically be 24 gauge. The distal end 30 of the body is provided with a smooth rounded tip 31 which will slide smoothly down the esophagus or guide tube (if used).

When the electrode 10 is used to stimulate breathing, the distal end 30 is positioned so that the several ring contacts 24 lie in the lower third of the esophagus. The stop 20 ensures proper positioning of the electrode.

The external electrodes 12 and 14 are identical and may be like those used in electrocardiogram machines. Each includes a flat circular pad 32 with a post contact 34 on its upper surface connected to electrical contact 36 on its lower surface. A conducting gelatin is applied to the contact 36 when in use to make good electrical contact with the patient's skin. The under surface of the pads 32 may also carry an adhesive to secure the electrodes in place on the patient's chest on each side, in the region of the fourth ribs. The post contacts 34 may be engaged- by snaps 38 which connect the electrodes 12 and 14 to the electrical circuit 16.

Figure 5:
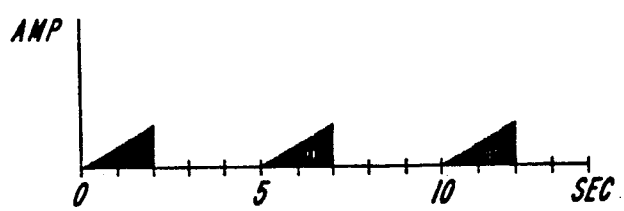
FIG. 5 is a chart of one pulse pattern that may be impressed upon the patient in accordance with this invention.
Figure 6:
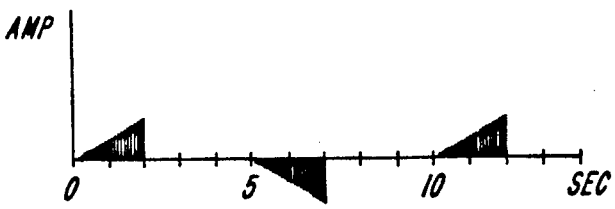
FIG. 6 is a chart similar to FIG. 5 but showing another pulse pattern that may be impressed upon a patient in accordance with this invention.
Figure 4:
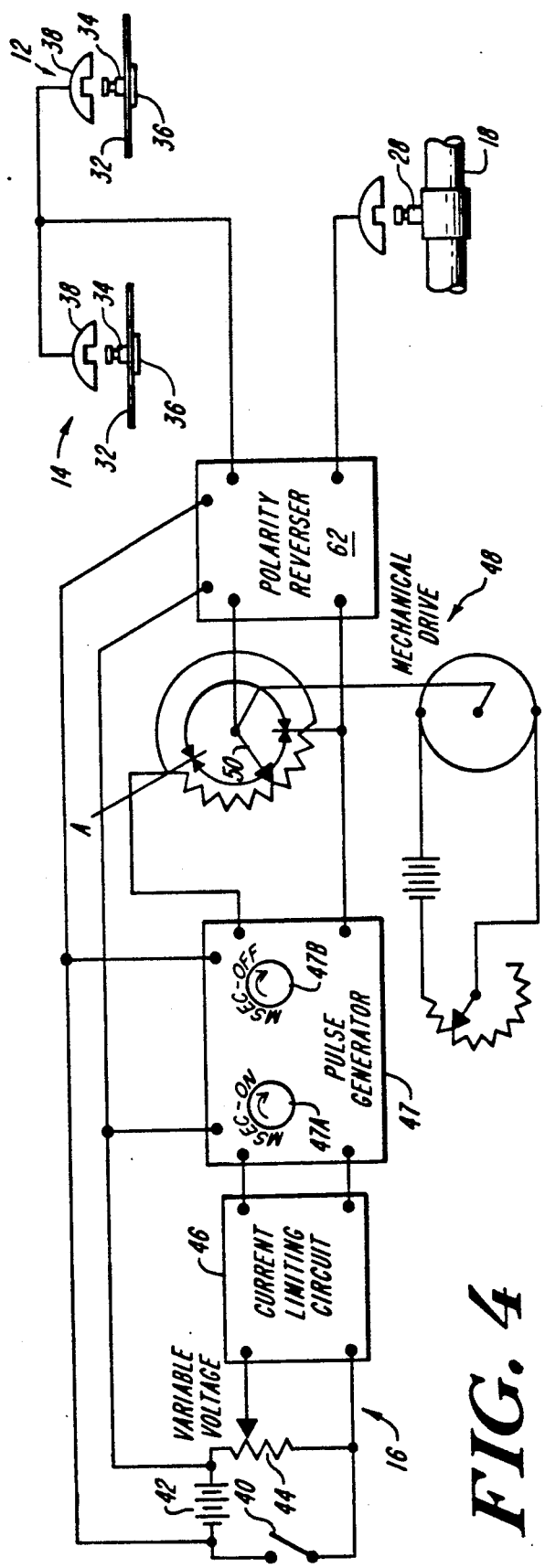
FIG. 4 is a schematic diagram of the circuit of the invention shown in FIGS. 1–3.
Figure 7:
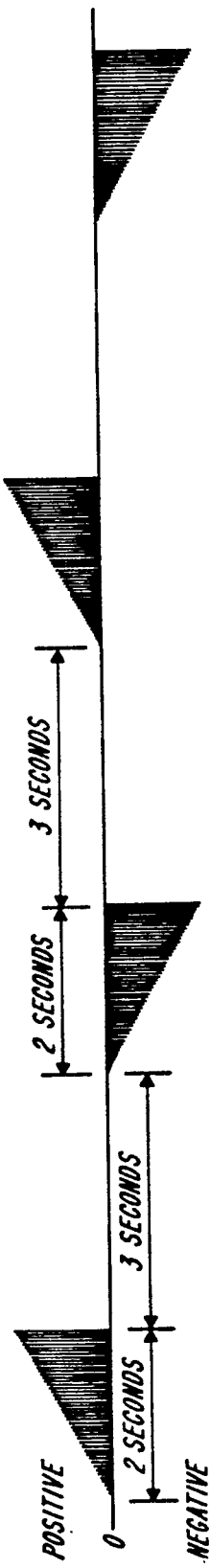
FIG. 7 is an enlarged fragmentary view of a series of pulses in one stimulation in the patterns of FIGS. 5 and 6.

The control circuit 16 for impressing a pulsed electrical stimulation across the electrodes is shown in FIG. 4. The circuit includes switch 40 and a battery 42 in circuit with a voltage divider 44 which enables the operator to select the desired current to be delivered. For the safety of the patient, a current limiting circuit represented by box 46 is connected across the output of the voltage divider. A pulse generator 47 powered from the main source 42 converts the direct current selected into a pulsing D.C. current. With controls 47A and 47B, the duration or "on" period of each pulse and the "off" period between the pulses ma be selected Typically, the "on" period of each pulse will be between 0.1–0.3 milliseconds and the "off" period will be from 1.0 millisecond to 2.0 milliseconds. This pattern is shown in the enlarged view of FIG. 7. A saw tooth generator in the form of a motor driven continuously rotating potentiometer 48 is connected across the voltage divider to produce the saw tooth signals shown in FIGS. 5 and 6. This signal may be processed through the polarity reverser 62 which is also powered from the main source if it is desired to reverse the polarity of the stimulations as suggested, for example, in FIG. 6. The internal electrode 10 and external electrodes 12 and 14 in turn ar connected to the output of the polarity reverser 62.

Using short 0.1 millisecond pulses, the heart cells are not activated, so heart arrhythmia or other heart malfunctions are not induced. The ramp configuration of the electrical stimulation is composed of a train of voltage pulses, each 0.1 millisecond in duration followed by an "off" or zero voltage period of 1 millisecond, the first voltage pulse is of very low amplitude with each succeeding pulse increasing in amplitude for a total period of time of approximately 2.0 seconds, at which time the voltage, having increased in linear fashion, will be approximately 70 volts. All stimulation then ceases for approximately 3 seconds at which time the stimulation cycle is repeated, preferably in a reversed polarity from the preceeding stimulation as suggested in the diagram of FIG. 6.

The foregoing describes a stimulation rate of twelve ventilations per minute with a voltage of 70 volts. Of course, if other ventillation rates and voltages are required, they are available from the instrument.

The ramp configuration of short duration pulses is efficient for stimulating the nerves and muscles associated with breathing. The patient breathes in a manner duplicating normal breathing; i.e.—the chest smoothly expands creating negative pressure in the lungs, and the ambient pressure air fills the lungs. When the electrical stimulation ceases, the muscles return the chest and lungs to the normal position exhaling the air.

If nerves and muscles are electrically stimulated only with a positive voltage, after a short period of time, their response diminishes, because it appears that they gradually assimilate a little of the charge and do not return to zero. The charge continues to build up so that more voltage is required to maintain control, and within a few minutes control may be lost. The same is true if only negative voltage is used. However, if the polarity is reversed at each cycle the muscles or nerves are forced to discharge the small assimilated charge as part of its acceptance of the new reversed voltage. The muscles and nerves may then be continuously stimulated with maximum effect.

In accordance with the present invention, as the pulses of each stimulation pass between the internal and external electrodes, the thoracic activity expands to create a negative pressure, and inspiration occurs. Between stimulations, the muscles relax to cause exhalation. This normal way of breathing does not inhibit blood flow in the lungs and to the heart.

In accordance with the method of this invention, the electrical stimulation is directed between an internal electrode placed in the esophagus and external electrodes placed on the chest in the region of the fourth ribs, and the charge serves to stimulate the diaphragm muscles so as to cause the lungs to expand. This technique is practiced without requiring any surgical procedure and therefore may be conducted by a paramedic. As the system is portable, the procedure may be carried out at any location. It does not require large, heavy equipment such as oxygen bottles, etc. The person administering the care may very quickly insert the internal electrode in place, affix the external electrodes at the desired locations and activate the pulsing circuit by closing the switch.

Having described this invention in detail, those skilled in the art will appreciate that numerous modifications may be made of this invention without departing from its spirit. Therefore, it is not intended that the scope of this invention be limited to the specific embodiment illustrated and described. Rather, the scope of the invention is to be determined by the appended claims and their equivalents.

What is claimed is:

1. A method of stimulating breathing in humans comprising the steps of
   positioning adjacent the sides of the chest muscles of a patient a non-invasive internal electrode within the body and external electrodes outside the body of the patient,
   imposing successive electrical pulsed stimulations between the internal electrode and external electrodes for causing the thoracic cavity to expand with each stimulation and relax between stimulations at the rate of between 10 and 18 times per minute, and periodically reversing the polarity of the pulsed stimulations,
   wherein each said pulsed stimulation includes a set of successive pulses of increasing magnitude over the duration of each pulsed simulation and the amplitude and duration of each pulsed stimulation is the same.

2. A method of stimulating breathing in humans as defined in claim 1 wherein
   the polarity of the stimulation is reversed on each successive cycle.

3. A method of stimulating breathing in humans as defined in claim 1 wherein
   the magnitude of successive pulses in each pulsed stimulation is increased gradually to a maximum value followed by an abrupt secession of the pulses.

4. A method of stimulating breathing in humans as defined in claim 1 wherein
   a period of no stimulation is interposed between successive stimulations, and wherein the duration of each stimulation is approximately two seconds and a period of approximately three seconds without stimulation is interposed between the successive stimulations.

5. A method of stimulating breathing in humans as defined in claim 4 wherein
   the magnitude of successive pulses is increased gradually to a maximum value followed by an abrupt secession of the pulses.

6. A method of stimulating breathing in humans as defined in claim 4 wherein
   the polarity of the stimulations is reversed on each successive cycle.

7. A method of stimulating breathing in humans as defined in claim 1 further characterized by
   adhering the external electrodes to the skin by an electrically conductive adhesive.

8. A method of stimulating breathing in humans as defined in claim 7 further characterized by
   using ECG-type electrodes as the external electrodes.

9. A method of stimulating breathing in humans as defined in claim 1 further characterized by
   causing said successive pulses to increase in magnitude from zero to a maximum over a period of approximately two seconds and delaying the first pulse of each stimulation to start approximately three seconds after the last pulse of the next preceding stimulation.

10. Medical apparatus for inducing breathing in humans comprising
    an internal elongated first electrode member for insertion into the esophagus,
    ECG-type external second and third electrode members for placement on the chest in the region of the lowermost ribs,
    and electrical circuit means connected to the three electrode member for passing an electrical stimulation current between the internal and external electrode members at a rate of between 10 and 18 stimulations per minute with each stimulation having a duration of approximately two seconds and a value of approximately 100 milliamperes.
    wherein each electrical stimulation is of substantially the same duration and magnitude and includes a set of successive pulses, and said electrical circuit means includes means for increasing the magnitude of each successive pulse in each electrical stimulation and wherein the circuit means further includes a polarity reversing module for periodically reversing the polarity of the stimulations.

11. Medical apparatus as defined in clainm 10 wherein said electrical circuit means includes means for increasing the magnitude of the successive pulses of each stimulation from zero to a maximum value gradually over the duration of each stimulation.

12. Medical apparatus for inducing breathing in humans comprising
    a first internal electrode means for insertion into the esophagus of a patient and having a distal end with an electrical contact to be positioned in the lower third of the esophagus, external electrode means having contact means for placement on the chest adjacent the diaphragm muscles, and electrical circuit means connected to the electrode means for imposing successive pulsed stimulations of the same wave shape, duration and amplitude between the internal and external electrode means, each stimulation being of approximately two seconds duration and with approximately three seconds between stimulations and limited to a maximum current of approximately 100 milliamperes for stimulating the diaphragm to cause the patient to breath.

wherein each said pulsed stimulations includes a set of successive pulses, said circuit means further includes a polarity reversing module for periodically reversing the polarity of the stimulations.

13. Medical apparatus as defined in claim 12 wherein the circuit means includes a polarity reversing module for periodically reversing the polarity of the stimulations.

* * * * *